US00PP16027P2

(12) United States Plant Patent
van Kesteren

(10) Patent No.: US PP16,027 P2
(45) Date of Patent: Oct. 11, 2005

(54) ***CAMPANULA* PLANT NAMED 'PURPLE SENSATION'**

(50) Latin Name: ***Campanula* hybrid**
Varietal Denomination: Purple Sensation

(76) Inventor: Mark van Kesteren, Westeinde 32, Noordwijkerhout 2211 XP (NL)

( * ) Notice: Subject to any disclaimer, the term of this patent is extended or adjusted under 35 U.S.C. 154(b) by 151 days.

(21) Appl. No.: 10/935,970

(22) Filed: Sep. 7, 2004

(51) Int. Cl.[7] ..... A01H 5/00
(52) U.S. Cl. ..... Plt./263
(58) Field of Search ..... Plt./263

*Primary Examiner*—Anne Marie Grunberg
(74) *Attorney, Agent, or Firm*—Penny J. Aguirre

(57) ABSTRACT

A new cultivar of hybrid *Campanula*, 'Purple Sensation', characterized by deep purple colored flowers, dark green foliage and purple stems. 'Purple Sensation' is hardy to USDA Zone 3 and is shorter in height than is typical for this type of *Campanula*.

2 Drawing Sheets

Botanical classification: *Campanula* hybrid.
Cultivar designation: 'Purple Sensation'.

BACKGROUND OF THE INVENTION

The present invention relates to a new and distinct cultivar of hybrid *Campanula* plant, botanically known as *Campanula* 'Purple Sensation' and will be referred to hereafter by its cultivar name, 'Purple Sensation'. The new cultivar represents a new Bellflower, an herbaceous perennial grown for landscape use.

The inventor discovered the new cultivar, 'Purple Sensation', in a cultivated growing area at his nursery in Noordwijkerhout, The Netherlands in the summer of 2000. 'Purple Sensation' originated as a chance seedling and the parentage is unknown.

The new cultivar is most similar in plant habit and flower form to the cultivar *Campanula* 'Kent Belle' (unpatented), a hybrid between *Campanula takesimana* and *Campanula latifolia* and 'Kent Belle' is presumed to be of similar origin. 'Purple Sensation' differs from 'Kent Belle' in having darker green foliage, darker purple flowers and a shorter plant height.

Asexual reproduction of the new cultivar was first accomplished by stem cuttings in Noordwijkerhout, The Netherlands in spring of 2001 by the inventor. Propagation by stem cuttings and tissue culture has determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'Purple Sensation' from other varieties of *Campanula* known to the inventor.

1. Dark green foliage.
2. Very deep colored purple flowers.
3. Purple stems.
4. Reaches a height of 60 cm and a spread of about 40 cm.
5. Cold hardy to USDA Zone 3.

BRIEF DESCRIPTION OF THE DRAWING

The accompanying colored photographs illustrate the overall appearance and distinct characteristics of the new *Campanula*. The photographs were taken in June of one year-old plants grown in a one gallon container in The Netherlands.

The photograph in the first sheet is a view of a plant of 'Purple Sensation' in bloom.

The photograph on the top of the second sheet is of a close-up view of the flowers of 'Purple Sensation' while the photograph on the bottom of the second sheet is a close up view of the foliage.

The colors in the photographs are as close as possible with the photographic and printing technology utilized. The color values cited in the detailed botanical description accurately describe the colors of the new *Campanula*.

DETAILED BOTANICAL DESCRIPTION OF THE PLANT

The following is a detailed description of 12 month-old, field grown plants of the new cultivar as grown outdoors in Boskoop, The Netherlands under natural lighting without supplemental watering and average temperatures of 12° C. to 25° C. (day) and 4° C. to 14° C. (night). The phenotype of the new cultivar may vary with variations in environmental, climatic and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

Botanical classification: 'Purple Sensation' is a cultivar of *Campanula* of hybrid origin.

Parentage: Naturally occurring chance seedling of unknown parentage.

*Blooming period.*—Mid June to early July in The Netherlands.

*Plant habit.*—Herbaceous perennial, narrow upright flowering habit that arise from basal foliage.

*Height and spread.*—Reaches about 60 cm in height and about 40 cm in spread.

*Cold hardiness.*—USDA Zone 3.
*Heat tolerance.*—At least tolerant to temperature up to 30° C.
*Culture.*—Grows best in neutral to alkaline, moist but well-drained soils in full sun to partial shade.
*Diseases and pests.*—No susceptibility or resistance to diseases or pests has been observed for 'Purple Sensation'.
*Root description.*—Fibrous on creeping rootstock.
*Branching habit.*—Flowering stems are unbranched and arise from basal foliage.

Growth and propagation:
*Growth rate.*—Moderately vigorous.
*Propagation.*—In vitro propagation and stem cuttings.
*Time required for root development.*—10 days at 25° C. during the summer in a greenhouse without supplemental lighting.
*Time required for root development.*—Cropping time from a rooted liner is 20 weeks to fully develop in a 11 cm to 13 cm container.

Stem description:
*Stem size.*—Average of 36 cm in length (excluding inflorescence), 4 mm in width.
*Stem shape.*—Round.
*Stem color.*—Greyed-orange to yellow-green; 176A and 176B to 144B and 144C, base greyed-purple; 187A.
*Stem surface.*—Covered with strigose hairs, average of 1 mm in length, N155A in color.
*Internode length.*—Average of 2.3 cm.
*Other stem characteristic.*—Inulin present (milky sap), observed if stem is cut.

Foliage description:
*Leaf shape.*—Ovate to broadly elliptic.
*Leaf division.*—Simple.
*Leaf base.*—Cuneate.
*Leaf apex.*—Acute.
*Leaf venation.*—Pinnate, 144C to 144D in color on upper and lower surfaces.
*Leaf margins.*—Serrate (average of 2 teeth per cm).
*Leaf attachment.*—Sessile.
*Leaf arrangement.*—Alternate.
*Leaf surface.*—Upper and lower: densely covered (on underside mainly on veins) with stiff hispid hairs, about 1 mm in length, 157D in color.
*Leaf color.*—Young, upper: 137A with a lighter base 143B to 143C; Young, lower: 137B with a lighter base 143C; Mature, upper: 137B; Mature, lower: 138B.
*Leaf size.*—Average of 6 cm in length and 2.9 cm in width.
*Leaf quantity.*—Average of 14 per branch.
*Other foliage characteristic.*—Inulin present (milky sap), visible if cut or broken.

Flower description:
*Inflorescence type.*—Terminal raceme.
*Lastingness of inflorescence.*—About 2.5 weeks from the opening of the first flower to senescence of last flower, individual flowers last about 10 days, persistent.
*Flower size.*—Average of 19 cm in height and 11 cm in width.
*Flower fragrance.*—None.
*Flower number.*—Average of 10 per inflorescence, one inflorescence per stem.
*Flower aspect.*—Pendulous.
*Flower bud size.*—Average of 3.5 cm in length, up to 3.2 cm in width (including calyx).
*Flower bud color.*—Dark greyed-purple; in between N186A and N186C (closest to N186C).
*Flower bud shape.*—Oblong.
*Flower form.*—Campanulate.
*Flower size.*—Average of 7.5 cm in depth and 3.9 cm in width.
*Corolla features.*—Petals are partially fused into campanulate form.
*Petal number.*—5.
*Petal shape.*—Upper un-fused portion is ovate.
*Petal color.*—Opening: 86A on upper surface (inner) and lower (outer) surface; Fully open: 86A on upper surface, between 86A and N88A on lower surface (closest to 86A); Fading: to 92B and 92C.
*Petal surface.*—Moderately glossy, outer (under) side smooth, inner (upper) side hirsute with hairs about 2 mm in length, 155A in color.
*Petal margins.*—Entire.
*Petal apex.*—Acute.
*Petal size.*—Average of 6.3 cm in length and 2 cm in width (measured at the base of the free part of the petal).
*Calyx form.*—Rotate.
*Calyx size.*—Average of 1.5 cm in length and 4.9 cm in width.
*Sepal number.*—5.
*Sepal shape.*—Narrowly lanceolate.
*Sepal margin.*—Entire, very wavy at base.
*Sepal size.*—Average of 2.9 cm length, 8 mm in width.
*Sepal surface.*—Dull, rough to the touch due to pubescence (hairs have an average length of 1 mm and are N155A in color.
*Sepal apex.*—Acute.
*Sepal base.*—Cuneate, base of sepals fused.
*Sepal color.*—Opening: 137B to 137C on upper surface (inner) and 137A tinted with 176B on lower (outer) surface; Fully open: 137B on upper surface, and 137A tinted with 176B on lower surface.
*Peduncle size.*—Average of 19 cm in length (length of inflorescence) and 3 mm in diameter.
*Peduncle strength/aspect.*—Strong, held upright.
*Peduncle shape.*—Round.
*Peduncle color.*—144A to 144B.
*Petiole size.*—Average of 3.5 cm in length and 1.5 mm in width.
*Petiole shape.*—Round.
*Petiole strength/aspect.*—Strong, lateral flowers are held at about 30° relative to stem.
*Petiole color.*—144A.

Reproductive organs:
*Gynoecium.*—1 pistil, about 3.5 cm in length, stigma is terete in shape with reflexed tips and 150C to 150D in color, style is about 3 cm in length,155B in color, base of style is covered with 5 sepal-like leaves (broadly ovate in shape, retuse apex, cuneate base, 4 mm in length and width, N155A in color and densely covered with white hairs 1 mm in length and N155A in color, ovary is 143B in color.
*Androcoecium.*—5 stamens, anthers are basifixed, narrowly oblong in shape, curled, and 8 mm in length, filament is 3 mm in length, pollen is low in abundant and 11C to 11D in color.
*Fruit/seeds.*—No fruit set (or seeds) were observed.

I claim:

1. A new and distinct cultivar of *Campanula* plant named 'Purple Sensation' as herein illustrated and described.

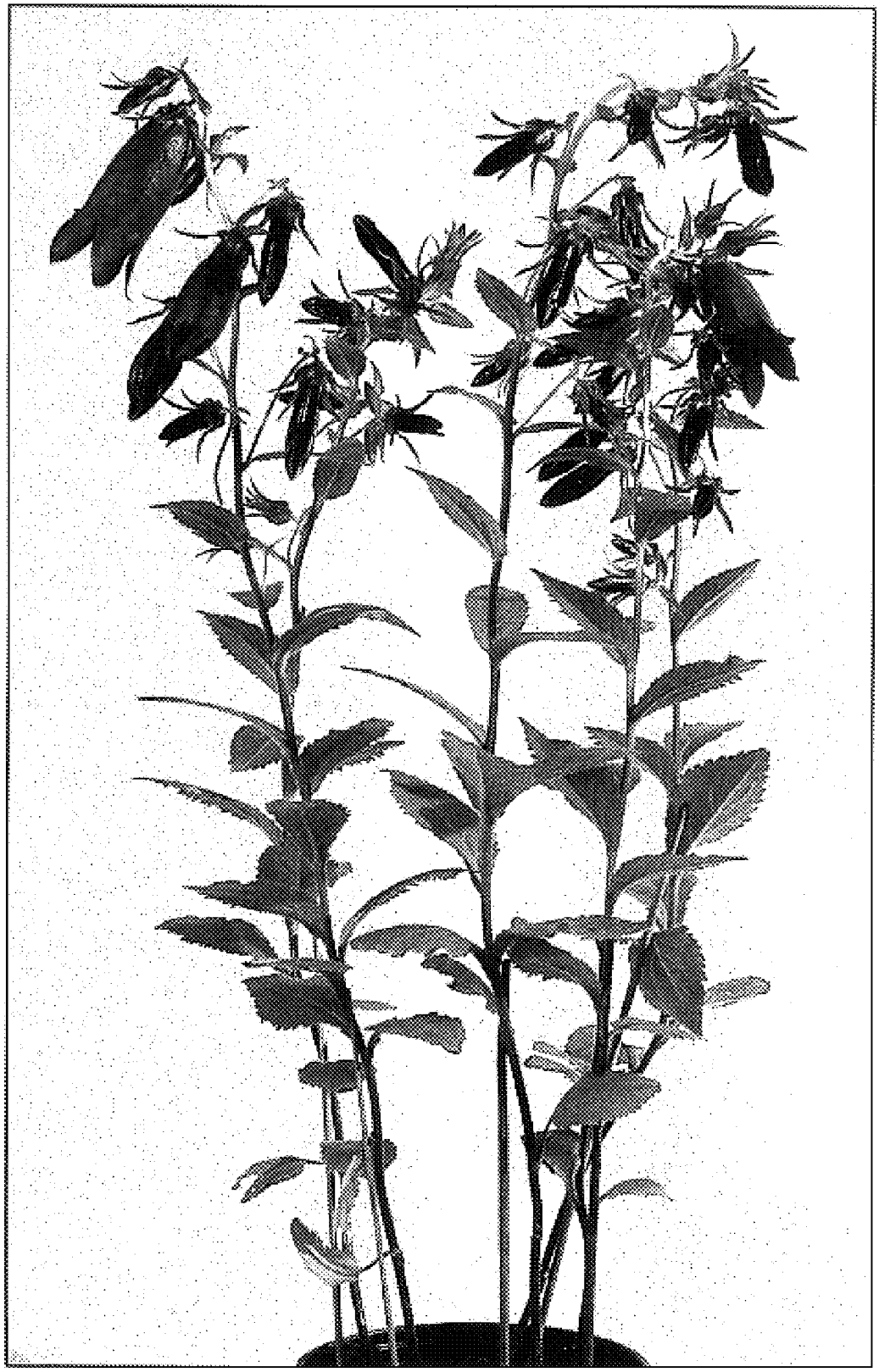

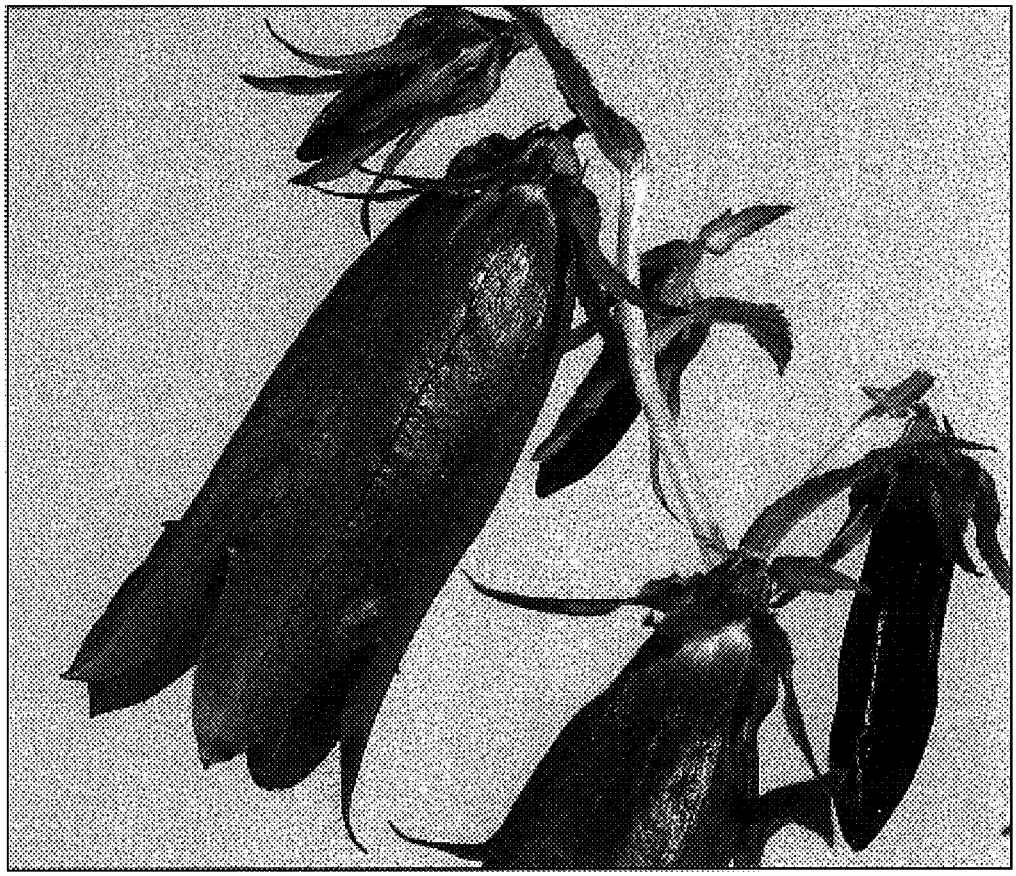
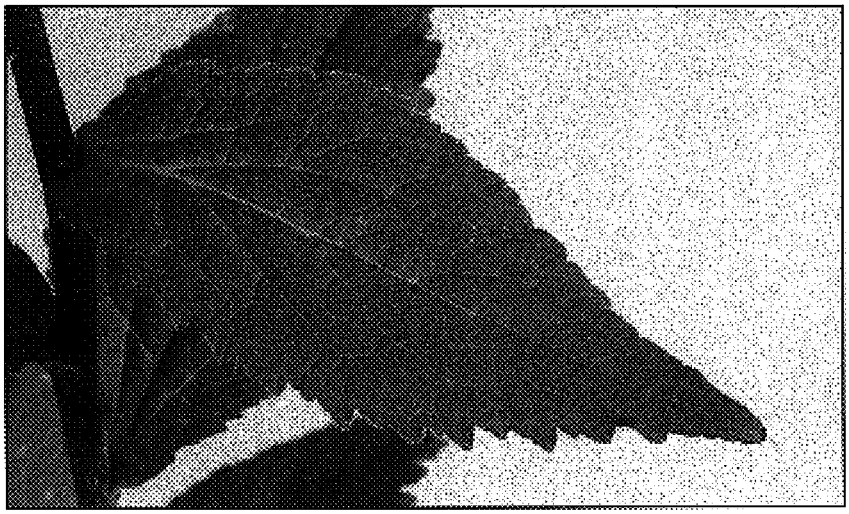

* * * * *